(12) United States Patent
Coates

(10) Patent No.: US 9,586,024 B2
(45) Date of Patent: Mar. 7, 2017

(54) GUIDE CATHETER WITH RADIOPAQUE FILAMENTS FOR LOCATING AN OSTIUM

(75) Inventor: Paul Coates, Corte Madera, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1100 days.

(21) Appl. No.: 13/088,712

(22) Filed: Apr. 18, 2011

(65) Prior Publication Data

US 2012/0265056 A1 Oct. 18, 2012

(51) Int. Cl.
*A61B 5/05* (2006.01)
*A61M 25/01* (2006.01)

(52) U.S. Cl.
CPC . *A61M 25/0108* (2013.01); *A61B 2090/3966* (2016.02)

(58) Field of Classification Search
USPC .......... 600/424, 423, 426, 431–435, 462, 600/466–467; 604/104
See application file for complete search history.

(56) References Cited

U.S. PATENT DOCUMENTS

| | | | |
|---|---|---|---|
| 3,687,142 A | 8/1972 | Leibinzohn | |
| 5,601,538 A | 2/1997 | Deem | |
| 5,695,469 A * | 12/1997 | Segal | 604/104 |
| 5,749,890 A | 5/1998 | Shaknovich | |
| 5,899,890 A | 5/1999 | Chiang et al. | |
| 5,944,712 A * | 8/1999 | Frassica et al. | 604/529 |
| 6,221,059 B1 | 4/2001 | Chiang et al. | |
| 6,264,679 B1 | 7/2001 | Keller et al. | |
| 6,293,958 B1 | 9/2001 | Berry et al. | |
| 6,530,934 B1 | 3/2003 | Jacobsen et al. | |
| 7,801,627 B2 | 9/2010 | Haldeman | |
| 2002/0042651 A1* | 4/2002 | Liddicoat et al. | 623/2.11 |
| 2002/0099431 A1* | 7/2002 | Armstrong et al. | 623/1.11 |
| 2004/0073282 A1* | 4/2004 | Stanish | 623/1.3 |
| 2004/0111143 A1 | 6/2004 | Fischell et al. | |
| 2004/0143287 A1* | 7/2004 | Konstantino et al. | 606/194 |
| 2004/0153118 A1* | 8/2004 | Clubb et al. | 606/200 |
| 2005/0101968 A1 | 5/2005 | Dadourian | |
| 2008/0281230 A1* | 11/2008 | Kinoshita et al. | 600/585 |
| 2009/0054968 A1 | 2/2009 | Bonhoeffer | |
| 2009/0264988 A1* | 10/2009 | Mafi et al. | 623/1.23 |
| 2011/0245665 A1* | 10/2011 | Nentwick | 600/433 |

* cited by examiner

*Primary Examiner* — Joel F Brutus

(57) ABSTRACT

Flexible radiopaque filaments coupled to and extending from a distal end of a guide catheter are disclosed that aid a clinician in locating an ostium of a branch vessel. The filaments are at least partially formed of a radiopaque material and are designed to move with the blood flow. In a method of locating an ostium of a branch vessel or a fenestration of an implanted graft, at least some of the filaments enter the ostium or fenestration when the distal end of the guide catheter is placed proximal thereto. The filaments provide an accurate and quick indication of the ostium location without the need for a contrast agent.

20 Claims, 5 Drawing Sheets

GUIDE CATHETER WITH RADIOPAQUE FILAMENTS FOR LOCATING AN OSTIUM

FIELD OF THE INVENTION

The invention relates to a guide catheter, and more particularly, to a guide catheter having flexible radiopaque filaments for locating an ostium.

BACKGROUND OF THE INVENTION

Guide catheters are used to place diagnostic catheters, treatment catheters, electrode leads and the like in desired locations within the body of a patient. A guide catheter typically includes an elongated sheath that is inserted into a blood vessel or another portion of the body. A second catheter or lead is introduced through a lumen defined by the sheath. To enable precise positioning of a second catheter or lead, the guide catheter sometimes incorporates a radiopaque marker or radiopaque material to promote visibility. Using fluoroscopic imaging techniques, the physician can visualize the radiopaque portion of the guide catheter and place the second catheter or electrode lead in a desired position.

One particular area within the vasculature that may be difficult to locate is an ostium of a vessel. The ostium of a vessel is an opening, aperture, or orifice located at the point of origin of the vessel. Typically, a vessel branches off from a larger parent or main vessel. For example, the aorta gives rise to the coronary arteries; the opening at the origin of each coronary artery as it branches from the aorta is referred to as an ostium. It may be desirable to locate the ostium of a branch vessel in order to access the branch vessel, such as when treating a lesion or antherosclerotic plaque located within the branch vessel. It also may be desirable to locate the ostium of a branch vessel when a lesion is located at the ostium, e.g., an ostial lesion. It may also be desirable to locate a fenestration of a previously-implanted graft that aligns with an ostium of a branch vessel or an ostium of a re-directed internal mammary artery or a grafted saphenous vein. In any case, an operator often utilizes a guide catheter to locate a target ostium within the body.

When locating a target ostium, radiopaque contrast liquid is often injected into the patient and X-ray is utilized to visualize the vasculature and ostium location. Although contrast liquid may be effective in locating the ostium, contrast is cytotoxic and high amounts thereof can lead to contrast-induced nephropathy and complications with the patient such as renal failure. In addition, an ostium may be particularly difficult to locate due to a non-standard location or the individual anatomy of the patient, thus leading to repeated injections of contrast and higher X-ray exposure for the patient as well as higher X-ray exposure for the entire staff in the operating room. Since the contrast agent is cytotoxic, the administered amount is monitored and if a threshold limit is reached prior to successfully locating the target ostium, the procedure must nonetheless be stopped.

Accordingly there is a need in the art for improvements for locating a target ostium. Embodiments hereof relate to an ostium locating system for quickly and accurately locating a target ostium without requiring the use of a contrast agent or at least reducing the quantity of the contrast agent and minimizing X-ray exposure.

BRIEF SUMMARY OF THE INVENTION

Embodiments hereof are directed to a system for locating an ostium. The system includes an elongated device configured for advancement within a vasculature, and a plurality of filaments coupled to and extending from a distal end of the elongated device. The filaments are sufficiently flexible to be moved by blood flow through the vasculature and at least a portion of each filament is radiopaque.

Embodiments hereof are also directed to a method for locating an ostium. An elongated device is percutaneously advanced within a vasculature. A plurality of filaments are coupled to and extend from a distal end of the elongated device, and at least one of the plurality of filaments has at least a distal portion that is radiopaque. When the distal end of the elongated device is located proximate to an ostium, at least one of the filaments is moved by blood flow into the ostium.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary and renal arteries, the invention may also be used in any other body passageways where it is deemed useful. Furthermore, there is no intention to be bound by any expressed or implied theory presented in the preceding technical field, background, brief summary or the following detailed description.

Embodiments hereof relate to a guide catheter or other intravascular device having flexible radiopaque filaments that are designed to move with blood flow. The filaments are utilized for locating an ostium, wherein at least some of the filaments enter the ostium when the distal end of the guide catheter is placed proximally or distally adjacent to the ostium depending on whether an antegrade or retrograde approach is taken to the treatment site. By taking advantage of the natural path of blood flow within the vasculature, the flexible radiopaque filaments provide an accurate indication of the ostium location without the need for a contrast agent. In addition, by quickly locating the ostium and not requiring repeated injections of contrast agent, the flexible radiopaque filaments minimize X-ray exposure to both the patient and all other persons in the operating room.

Figure 1A:
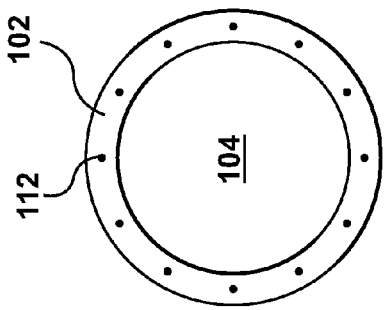
FIG. 1A is a cross-sectional view of the ostium locator system of FIG. 1 taken along line A-A of FIG. 1.
Figure 1:
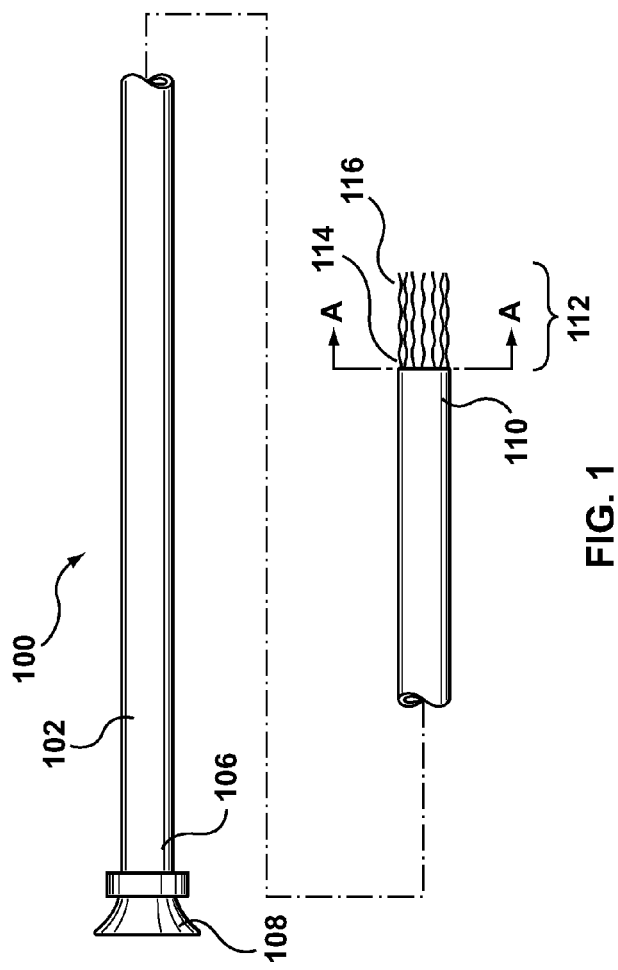
FIG. 1 is a side view of an ostium locator system according to an embodiment hereof, wherein the ostium locator system includes a guide catheter and a plurality of radiopaque filaments distally extending from the guide catheter.

Referring to FIGS. 1 and 1A, a system 100 for locating an ostium is shown. Ostium locating system 100 includes a guide catheter 102 and a plurality of filaments 112 coupled to a distal end 110 of guide catheter 102. Guide catheter 102 is an elongated tubular member or sheath sized for insertion into a lumen, such as a blood vessel, within the human body. Guide catheter 102 defines a lumen 104 through which other elements such as catheters and electrode leads may be inserted. Guide catheter 102 has a fitting or hub 108 for attaching to a Tuohy-Borst adapter (not shown) at the site of entry into a body lumen, as would be known to one of ordinary skill in the art. Hub 108 is coupled to a proximal end 106 of guide catheter 102 that extends outside of a patient and may be manipulated by an operator. Suitable guide catheters that may be modified for use in embodiments hereof include those shown and described in U.S. Pat. No. 5,902,287 to Martin and U.S. Pat. No. 5,964,971 to Lunn, which are both presently assigned to the same assignee of the present disclosure and are both hereby incorporated by reference in their entirety.

Guide catheter 102 may be formed of a polymeric material, non-exhaustive examples of which include polyethylene, PEBA, polyamide and/or combinations thereof, either blended or co-extruded. Optionally, guide catheter 102 or some portion thereof may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like. In one embodiment, for example, at least a proximal portion of guide catheter 102 may be formed from a reinforced polymeric tube.

Although described in conjunction with a guide catheter, the plurality of filaments 112 described herein may be utilized with any elongated device configured for advancement within a vasculature. The plurality of filaments 112 distally extend from guide catheter 102 in order to locate an ostium of a branch vessel, a fenestration of an implanted graft that aligns with an ostium of a branch vessel, or another ostium occurring within the body. At least a portion of each filament 112 is formed from a radiopaque material which is visible with standard fluoroscopy techniques and filaments 112 are sufficiently flexible to be moved with blood flow through the vasculature.

In the figures, for illustrative purposes only, filaments 112 are depicted as wavy in order to convey that filaments 112 are sufficiently flexible to flap, ripple, wave or otherwise move with blood flow within the vasculature. Each filament 112 is a generally straight fiber-like strand of material having a proximal end 114 coupled to distal end 110 of guide catheter 102 and a distal end 116 unattached and spaced apart from guide catheter 102. As shown in FIG. 1A, filaments 112 are approximately equally spaced around the circumference of distal end 110 of guide catheter 102. FIG. 1A depicts twelve filaments 112 coupled to the distal end of the guide catheter, but it will be apparent to those of ordinary skill in the art that the number of filaments 112 may vary. In an embodiment, the number of filaments 112 may range between 4 and 20. Proximal ends 114 of filaments 112 may be coupled to guide catheter 102 via any suitable mechanical method, including but not limited to adhesive, heat bonding, or welding. In an embodiment, the length of each filament 112 may be approximately the same and may fall within a range between 0.5-4 cm. In another embodiment, filaments 112 may be of varying lengths.

Figure 2:
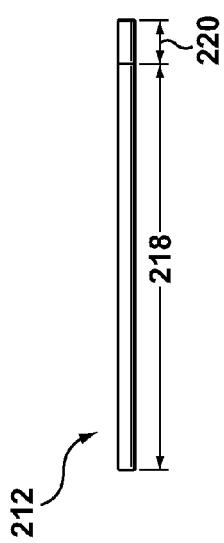
FIG. 2 is a side view of a filament according to another embodiment hereof, wherein the filament includes a polymeric proximal segment and a radiopaque distal tip.

In an embodiment shown in FIG. 1, filaments 112 are strands of radiopaque material visible under a fluoroscopic device. Non-exhaustive examples of heavy metals that are generally visible by X-ray fluoroscopy and thus suitable for forming filaments 112 include but are not limited to tantalum, titanium, platinum, gold, silver, palladium, iridium, rhenium, tungsten, and alloys containing one or more thereof. In another embodiment shown in FIG. 2, a proximal segment 218 of each filament 212 is a polymeric material or flexible metallic material having low radiopacity for providing the required flexibility and a distal segment or tip 220 is a radiopaque material such as those listed herein as being visible by X-ray fluoroscopy. Non-exhaustive examples of polymeric materials for proximal segment 218 of filaments 212 are polyurethane, polyethylene terephalate (PET), nylon, polyethylene, PEBAX, or combinations of any of these, either blended or co-extruded. In yet another embodiment hereof, each filament may be formed of a polymeric material with radiopaque particles, e.g., gold nanoparticles, embedded therein.

Each filament 112 may be solid or hollow, and may have any suitable cross-section including but not limited to circular, annular, oval, or rectangular. Radiopaque filaments 112 are sufficiently fine, e.g., of a sufficiently small diameter or cross-section which depends upon the type of radiopaque material utilized for the strands, to flap, ripple, wave or otherwise move with blood flow. In addition, filaments 112 are fine enough so as to be able to enter an ostium, such as but not limited to the ostium of the coronary artery or saphenous vein graft, without causing damage thereto. In various embodiments, filaments 112 may have a diameter or cross-section that ranges between 0.0005-0.0100 inch. In another embodiment, filaments 112 are tantalum strands having a diameter or cross-section of approximately 0.002 inch.

Figure 3:
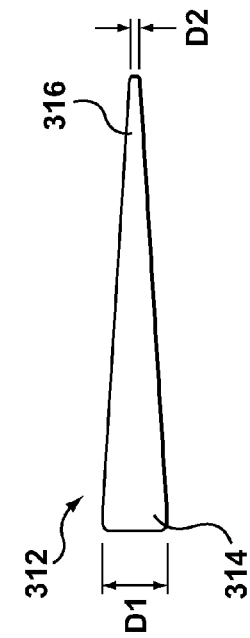
FIG. 3 is a side view of a filament according to another embodiment hereof, wherein the cross-section of the filament distally tapers.

Each filament may have a constant diameter or cross-section along its length, or may have a variable diameter or cross-section along its length. For example, as shown in FIG. 3, each filament 312 has a proximal end 314 having a diameter or cross-section D1 and a distal end 316 having a diameter or cross-section D2. Diameter D1 is greater than diameter D2 such that the outer diameter of each filament 312 tapers in a distal direction. A thicker proximal end 314 serves to provide more material for a secure connection between guide catheter 102 and filaments 312, while a thinner distal end 316 serves to provide the required flexibility of filaments 312.

Figure 4:
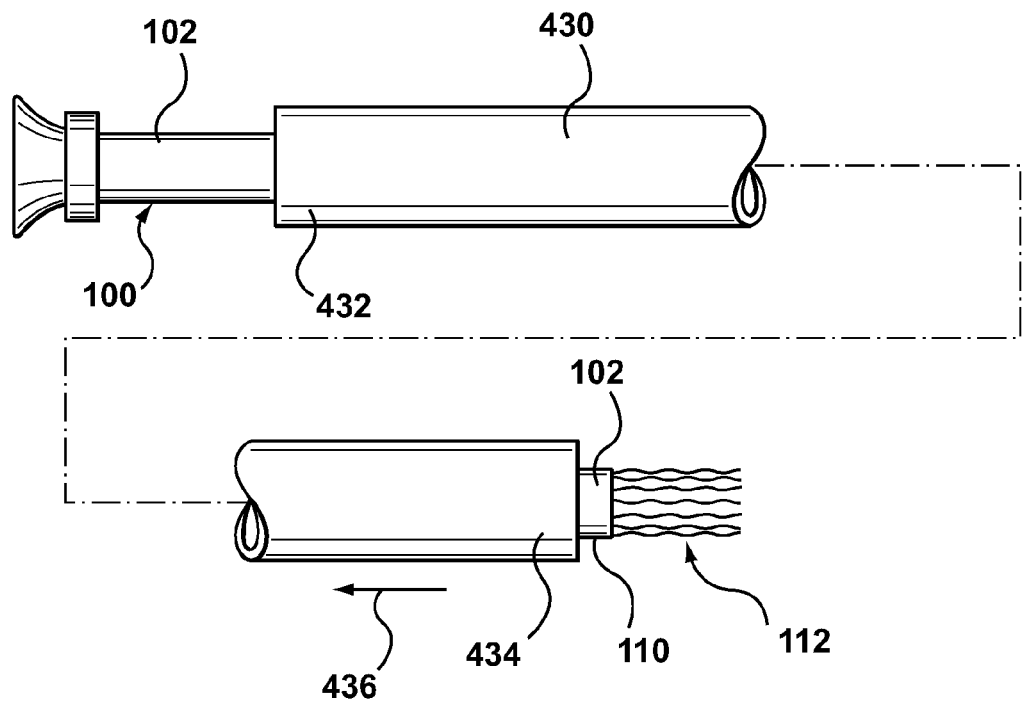
FIG. 4 is a side view of an ostium locator system according to another embodiment hereof, wherein an outer sheath is slidingly disposed over the ostium locator system of FIG. 1.

It may be desirable to shield or protect filaments 112 during delivery within the vasculature. In an embodiment shown in FIG. 4, an outer sheath 430 is slidingly disposed over guide catheter 102 and filaments 112. Outer sheath 430 is a tubular component having a single lumen (not shown), a proximal end 432 that extends outside of a patient and may be manipulated by an operator, and a distal end 434 that may be positionable at a target location within the vasculature. Outer sheath 430 allows for selective deployment and re-capture of filaments 112. Outer sheath 430 protects filaments 112 from entanglement or otherwise being damaged while ostium locating system 100 is being tracked within a tortuous vasculature. In FIG. 4, filaments 112 and distal end 110 of guide catheter 102 are shown protruding from distal end 434 of outer sheath 430, but it should be understood that this is for illustrative purposes only and that during delivery while outer sheath 430 is being advanced through the vasculature ostium locating system 100 would be maintained within the lumen of outer sheath 430 until deployment. After the distal end of the guide catheter is placed in the general area of the target ostium, filaments 112 are exposed by retracting sheath 430 in a direction indicated by directional arrow 436.

Figure 5:
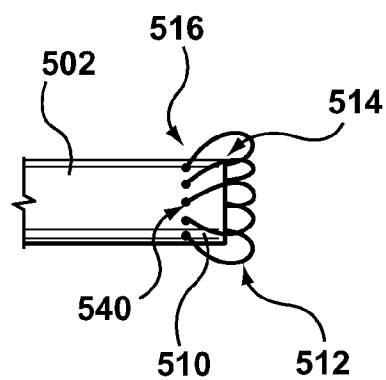
FIG. 5 is a side view of a distal portion of an ostium locator system according to another embodiment hereof, wherein at least a distal end of the filaments are releasably attached to the guide catheter.

In another embodiment hereof, the filaments may be temporarily and releasably attached to the guide catheter in order to shield or protect the filaments during delivery within the vasculature. More particularly, as shown in FIG. 5, a proximal end 514 of each filament 512 is permanently attached to a distal end 510 of a guide catheter 502 in the same way as described above with respect to proximal ends 314 of filaments 312. However, in this embodiment, each filament 512 forms a proximally-extending loop and at least a distal end 516 of each filament 512 is releasably attached to guide catheter 502 via a temporary bond 540. In one embodiment, temporary bond 540 includes a water soluble adhesive such that distal ends 516 of filaments 512 are released from guide catheter 502 upon exposure to the blood flow. After separation from guide catheter 502, filaments 512 elongate and move with blood flow as described herein in order to locate an ostium. In another embodiment (not shown), the length of filaments 512 may be temporarily and releasably attached to guide catheter 502 via a water soluble adhesive or other temporary bond.

Figure 6:
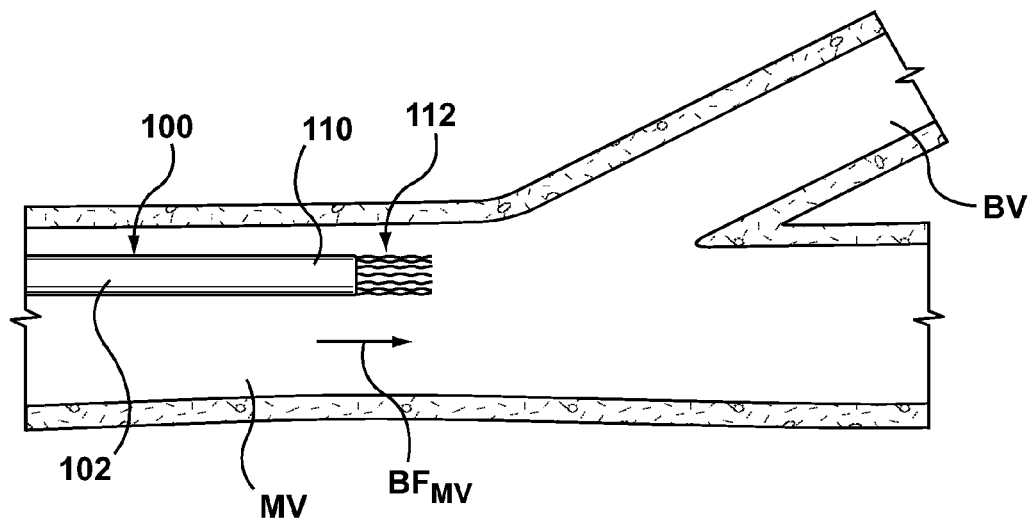
FIGS. 6-7 illustrate a method of locating an ostium of a branch vessel using the ostium locator system of FIG. 1.
Figure 7:
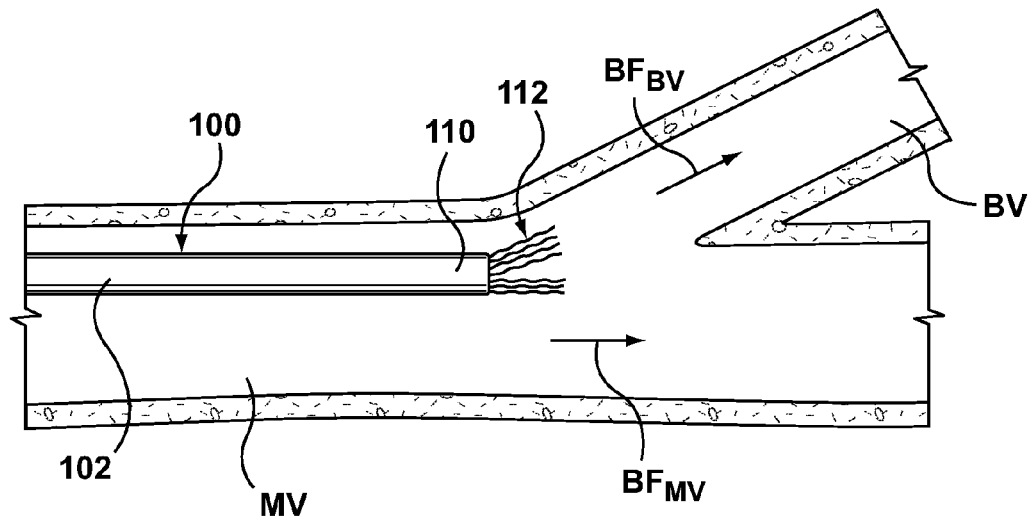

Turning now to FIGS. 6-7, a method of locating an ostium of a branch vessel BV using ostium locator system 100 is described. Branch vessel BV may be any vessel occurring in the body which branches off a main vessel. In one embodiment, branch vessel BV is a coronary artery. In another embodiment, branch vessel BV is a renal artery. Although described in relation to an ostium of a branch vessel, it should be understood that the methods and apparatus utilizing filaments 112 as described herein may be used to locate any ostium within a body. For example, the method may be utilized for locating a fenestration of a graft such as but not limited to a saphenous vein graft placed. Grafts are positioned within a main vessel and include one or more aperture(s) or fenestration(s) formed therein that align with the ostium of one or more branch vessel(s) and provide perfusion to the branch vessels. The method may also be utilized for locating an ostium of a re-directed or bypassed internal mammary artery. When embodiments hereof are used in the arterial system, guide catheter 102, which is shown and described in relation to FIG. 1, is first inserted through an incision (not shown) into one of, for e.g., a femoral, brachial and radial artery of a patient depending on whether the clinician is taking an antegrade or retrograde approach to the treatment site. For example, the Seldinger Technique may be utilized for percutaneously introducing guide catheter 102. It would be understood by one of ordinary skill in the art that the aforementioned access points provide access to the arterial system, and that when embodiments hereof are used in the venous system different entry points would be used. Guide catheter 102 is maneuvered through the vasculature to a treatment site, which in this instance is in the general area in which a main vessel MV intersects with a target branch vessel BV as shown in FIG. 6. When located within main vessel MV, filaments 112 distally extend from distal end 110 of guide catheter 102 and flap, flutter, ripple, wave or are otherwise move by the blood flow $BF_{MV}$ within the main vessel MV. The orientation or direction of filaments 112 thus depends upon the flow path of the local blood flow within the vasculature.

Distal end 110 of guide catheter 102 is advanced through and positioned within the main vessel MV until one or more filaments 112 indicate the location of the ostium. More particularly as shown in FIG. 7, as the operator moves distal end 110 of guide catheter 102 around within main vessel MV, filaments 112 move with the local blood flow $BF_{MV}$ of the main vessel MV until the filaments are placed proximate to the ostium. When distal end 110 is proximate to the ostium, one or more filaments 112 enter into the ostium of branch vessel BV due to the local blood flow $BF_{BV}$ of the branch vessel, thus providing an indicator to the operator as to the location of the ostium.

Figure 8:
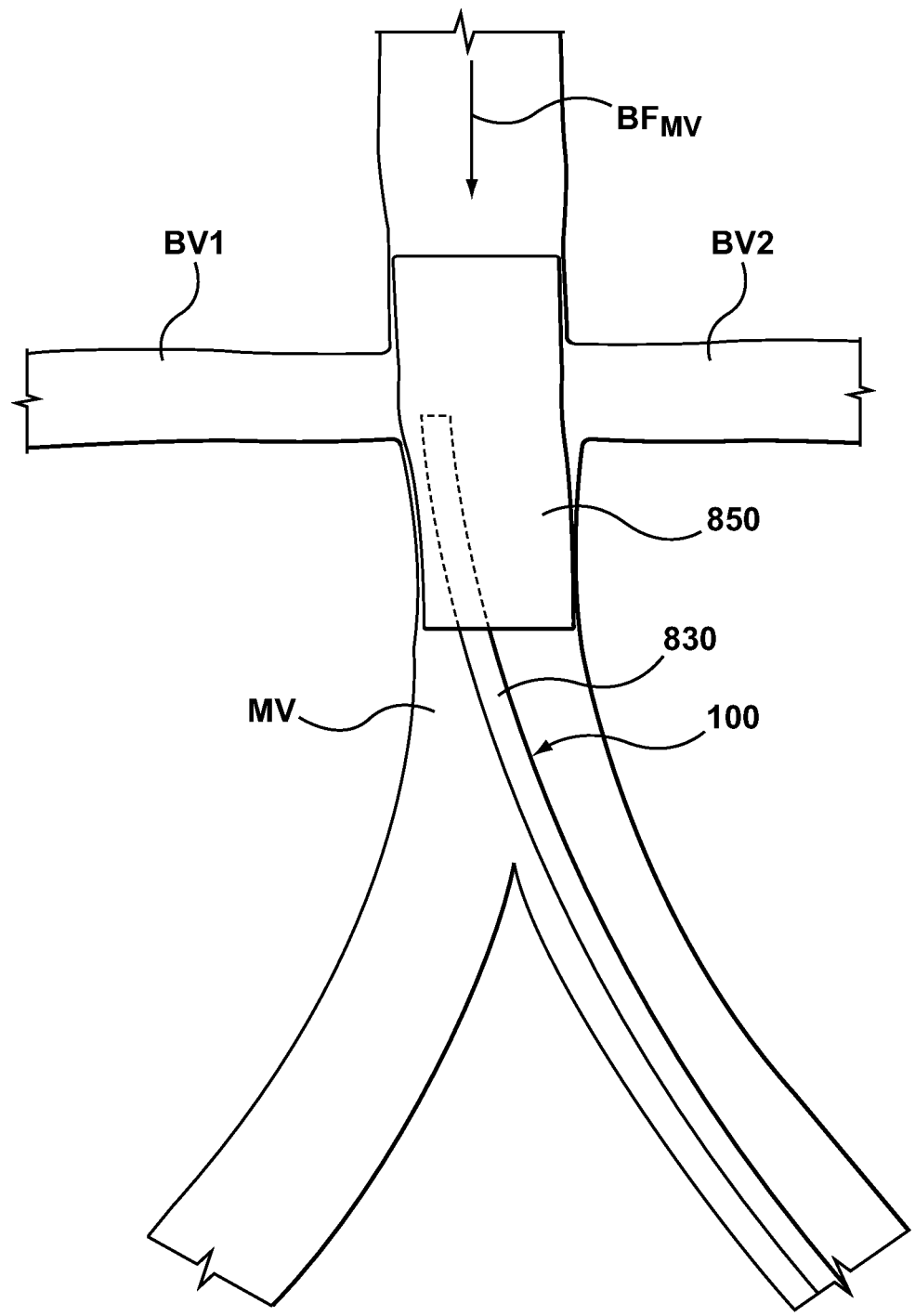
FIGS. 8-9 illustrate a method of locating a fenestration of a previously-implanted graft using the ostium locator system of FIG. 1.
Figure 9:
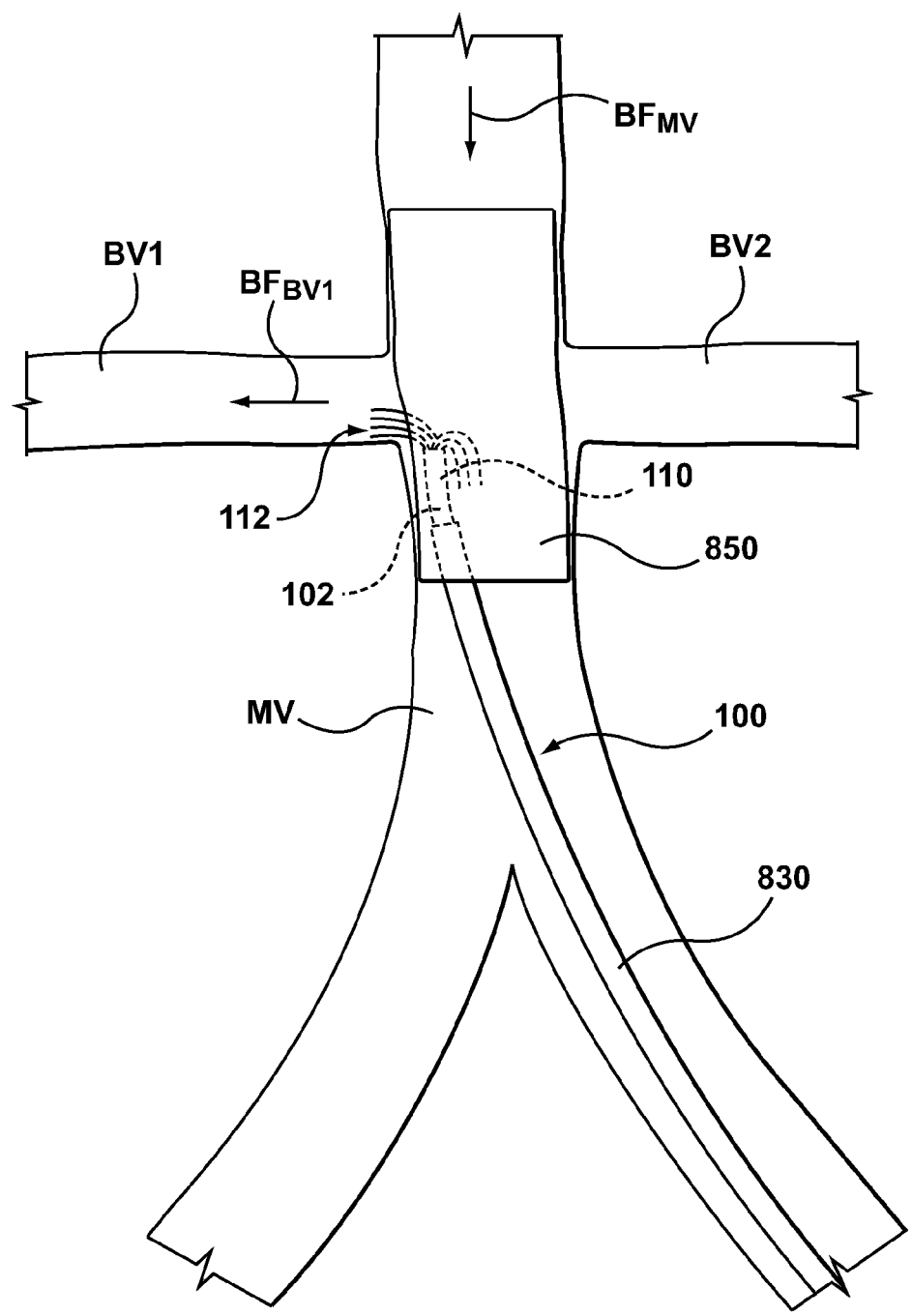

Turning now to FIGS. 8-9, a method of locating a fenestration of a previously implanted graft 850 using ostium locator system 100 is described. In this embodiment, graft 850 is an abdominal aortic graft implanted within the main vessel MV, the abdominal aorta. Graft 850 includes a target fenestration (not shown), i.e., an aperture or opening formed therein, for allowing blood flow to target branch vessel BV1, a renal artery. It will be understood by those of ordinary skill in the art that the methods and apparatus described herein may additionally or alternatively be utilized for locating a target fenestration formed in graft 850 that provides blood flow to the opposing renal artery, branch vessel BV2. Further, although described in relation to the renal arteries, it should be understood that the methods and apparatus utilizing filaments 112 as described herein may be used to locate an ostium occurring within any vessel or a fenestration of any graft implanted therein. In this embodiment, an outer sheath 830 is utilized to protect filaments 112 during delivery. Sheath 830 is particularly useful for protecting filaments 112 from damage in this embodiment because ostium locator system 100 is advanced in a retrograde approach, i.e., against the blood flow $BF_{MV}$ within the main vessel MV. Outer sheath 830 having guide catheter 102 inserted therein is first inserted through an incision (not shown) and into a femoral artery of a patient. As shown in FIG. 8, outer sheath 830 having guide catheter 102 inserted therein is maneuvered through the vasculature and through graft 850 to the general area of a treatment site, which in this instance is the fenestration of graft 850 that provides blood flow to branch vessel BV1.

Once positioned in the general area of the target fenestration, sheath 830 may be retracted to expose filaments 112. If necessary, distal end 110 of guide catheter 102 is moved around or repositioned within the main vessel MV until one or more filaments 112 indicate the location of the fenestration. More particularly as shown in FIG. 9, when distal end 110 is proximate to the fenestration of graft 850, one or more filaments 112 enter into the target branch vessel BV1 through the fenestration of graft 850 due to the local blood flow $BF_{BV1}$ of the branch vessel, thus providing an indicator to the operator as to the location of the graft fenestration. When filaments 112 locate the graft fenestration, filaments 112 also necessarily provide an indication to the operator as to the location of the branch vessel ostium since the graft fenestration is aligned with the ostium of target branch vessel BV1. As shown in FIG. 9, some of the filaments 112 may be directed by the blood flow $BF_{MV}$ within the main vessel MV and thus have a different orientation than those directed by blood flow $BF_{BV1}$ of the branch vessel.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A system for locating an ostium, the system comprising:
    an elongated device configured for advancement within a vasculature; and
    a plurality of filaments each having a proximal end coupled to a distal end of the elongated device and a distal end unattached to and spaced distally from the distal end of the elongated device in a deployed configuration, wherein the filaments are sufficiently flexible to be moved by blood flowing through the vasculature and wherein each of the plurality of filaments has at least a portion that is radiopaque.

2. The system of claim 1, wherein the elongated device is a guide catheter.

3. The system of claim 1, wherein the plurality of filaments are strands of radiopaque material.

4. The system of claim 3, wherein the radiopaque material is tantalum.

5. The system of claim 1, wherein at least one of the plurality of filaments is a polymer strand having a radiopaque distal tip.

6. The system of claim 5, wherein the radiopaque material is selected from the group consisting of tantalum, platinum, titanium, gold, silver, palladium, rhenium, iridium, tungsten, and alloys containing one or more thereof.

7. The system of claim 1, wherein at least one of the plurality of filaments has a constant cross-section along its length.

8. The system of claim 1, wherein at least one of the plurality of filaments has a distally tapering cross-section such that a proximal end of the filament has a larger cross-section than a distal end of the filament.

9. The system of claim 1, further comprising: a protective outer sheath slidingly disposed over at least the plurality of filaments.

10. The system of claim 1, wherein the distal end of at least one of the plurality of filaments is releasably attached to the elongated device with a water soluble adhesive in a delivery configuration.

11. A method for locating an ostium, the method comprising the steps of:
    percutaneously advancing an elongated device within a vasculature in one of an antegrade or retrograde direction, wherein a plurality of filaments are coupled to and extend distally from a distal end of the elongated device with at least a portion of each filament being radiopaque; and
    locating the distal end of the elongated device adjacent to an ostium, wherein at least one of the filaments is moved by blood flow towards the ostium.

12. The method of claim 11, wherein the elongated device is a guide catheter.

13. The method of claim 11, wherein at least one of the plurality of filaments is a strand of radiopaque material.

14. The method of claim 11, wherein at least one of the plurality of filaments is a polymer strand having a radiopaque distal tip.

15. The method of claim 11, wherein at least one of the plurality of filaments has a constant cross-section along its length.

16. The method of claim 11, wherein at least one of the plurality of filaments has a distally tapering diameter such that a proximal end of the filament has a larger diameter than a distal end of the filament.

17. The method of claim 11, further comprising the step of retracting a protective outer sheath which is slidingly disposed over at least the plurality of filaments.

18. The method of claim 11, wherein a distal end of at least one of the plurality of filaments is releasably attached to the elongated device with a water soluble adhesive.

19. The method of claim 11, wherein the ostium is an ostium of a branch vessel.

20. The method of claim 11, wherein the ostium is a fenestration of a graft.

* * * * *